United States Patent
Beller et al.

(10) Patent No.: US 6,297,270 B1
(45) Date of Patent: Oct. 2, 2001

(54) PROCESS FOR THE PREPARATION OF 2,3-DIHYDROINDOLES (INDOLINES), NOVEL 2,3-DIHYDROINDOLES, AND THEIR USE

(75) Inventors: Matthias Beller, Rostock; Thomas Riermeier, Flörsheim; Harald Trauthwein; Claudia Breindl, both of München, all of (DE)

(73) Assignee: Aventis Research & Technologies GmbH & Co. KG, Frankfurt am Main (DE)

( * ) Notice: Subject to any disclaimer, the term of this patent is extended or adjusted under 35 U.S.C. 154(b) by 0 days.

(21) Appl. No.: 09/442,615

(22) Filed: Nov. 18, 1999

(30) Foreign Application Priority Data

Nov. 20, 1998 (DE) .................................. 198 53 558

(51) Int. Cl.[7] .................... A61K 31/404; C07D 209/04
(52) U.S. Cl. ...................... 514/415; 548/490; 548/491
(58) Field of Search .................... 548/490, 491, 548/215, 239, 312.1; 514/415; 57/904; 424/47, 70.11, 78.36, 401; 502/152; 504/116.1; 520/1; 544/405; 546/122, 277.4

(56) References Cited

FOREIGN PATENT DOCUMENTS

07304972 * 5/1994 (JP) .

OTHER PUBLICATIONS

Beller et al., Angew Chem., Int. Ed. (1998), vol. 37, pp. 3389–3391, No. XP000882709.
R. Huisgen et al., Chemische Berichte, Bd. 92, 1959, pp. 424–429, No. XP000881378.
H. Iida et al., Journal of the Chemical Society Perkin Trans I, Bd. 23, 1975, pp. 2502–2506, No. XP00088168.

* cited by examiner

*Primary Examiner*—T.A. Solola
(74) *Attorney, Agent, or Firm*—Frommer Lawrence & Haug LLP

(57) ABSTRACT

A process for the preparation of 2,3-dihydroindoles of the formula (I)

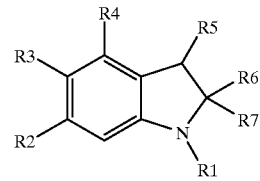

(I)

by reaction of halostyrenes of the formula (IIa) or (IIb)

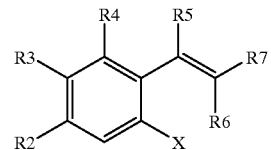

(IIa)

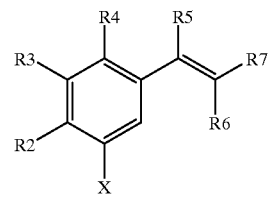

(IIb)

with amines of the formula (III)

$$R^1—NH_2$$ (III)

in at least one inert solvent or in water, and in the presence of at least one base.

33 Claims, No Drawings

PROCESS FOR THE PREPARATION OF 2,3-DIHYDROINDOLES (INDOLINES), NOVEL 2,3-DIHYDROINDOLES, AND THEIR USE

A large number of indole derivatives, in particular of indole alkaloids, are employed as medicaments in human and veterinary medicine (E. Breitmaier "Alkaloide: Betäubungsmittel, Halluzinogene und andere Wirkstoffe" [Alkaloids: Anesthetics, Hallucinogens and Other Active Compounds], Teubner Studienbücher Chemie, 1997). 2,3-Dihydroindole derivatives are likewise of great pharmocological interest as active compounds. Moreover, they serve as starting materials for corresponding indoles, since they can be very simply dehydrogenated (cf. B. Robinson, Chem. Rev. 1969, 69, 785; and also Y. Kikugawa, M. Kashimura, Synthesis 1982, 785).

In the university field, frequently used methods for the synthesis of indoles and 2,3-dihydroindoles are Fischer's indole synthesis (B. Robinson, Chem. Rev. 1969, 69, 227) and the Reissert reaction (G. Blasko, P. Kerekes, S. Makleit, Alkaloids (Academic Press) 1987, 31, 1–28; J. G. Cannon, B. J. Demopoulos, J. P. Long, J. R. Flynn, F. M. Sharabi, J. Med. Chem. 1981, 238–40).

The multistage reaction sequences can only be carried out with difficulty and are therefore industrially unimportant.

An alternative to this is the cyclization of halogen-substituted N-(2-arylethyl)amines via aryne intermediates (R. Huisgen, H. König, Chem. Ber. 1959, 92, 203; R. Huisgen, H. König, N. Bleeker, Chem. Ber, 1959, 92, 424; H. König, R. Huisgen, Chem. Ber. 1959, 92, 429; H. Iida, S. Aoyagi, C. Kibayashi, J. Chem. Soc., Perkin I 1975, 2502). The base employed in these reports is the compound phenyllithium, which is extremely reactive and difficult to handle industrially. The cyclization takes place only in yields of below 50%. As the 2-halophenylethylamines used as starting materials can only be obtained by a complicated multistage synthesis (total yields 13% and 18% respectively), this method also does not find any wide application.

The object of the present invention is the provision of a new preparation process for 2,3-dihydroindole derivatives which does not have the disadvantages of the known processes and is moreover suitable for carrying out on an industrial scale. A further object of the present invention is the provision of novel 2,3-dihydroindoles, and their use.

This object is achieved by a process for the preparation of 2,3-dihydroindoles of the formula (I)

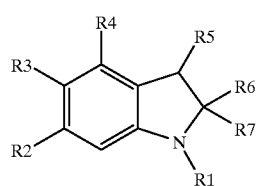

(I)

in which the radicals R1 to R7 independently of one another are selected from the group consisting of hydrogen, fluorine, chlorine, $(C_1-C_8)$-alkyl, O-alkyl-$(C_1-C_8)$, OCO-alkyl-$(C_1-C_8)$, OH, $NO_2$, Si(alkyl)$_3$-$(C_1-C_8)$, $CF_3$, CN, COOH, CHO, $SO_3H$, $NH_2$, NH-alkyl-$(C_1-C_8)$, N-alkyl$_2$-$(C_1-C_8)$, NH—Ar, NAr$_2$, P-alkyl$_2$-$(C_1-C_8)$, $SO_2$-alkyl-$(C_1-C_6)$, SO-alkyl-$(C_1-C_6)$, NHCO-alkyl-$(C_1-C_4)$, COO-alkyl-$(C_1-C_8)$, $CONH_2$, CONH-alkyl-$(C_1-C_8)$, CO-alkyl-$(C_1-C_8)$, NHCOH, NHCOO-alkyl-$(C_1-C_4)$, CHCH—$CO_2$-alkyl-$(C_1-C_8)$, $CHCHCO_2H$, P-alkyl$_2$-$(C_1-C_8)$, POalkyl$_2$-$(C_1-C_4)$, $PO_3H_2$, PO(O-alkyl-$(C_1-C_6)$)$_2$, $SO_3$-alkyl-$(C_1-C_4)$, $SO_2$-alkyl-$(C_1-C_6)$, SO-alkyl-$(C_1-C_6)$, Si(alkyl)$_3$-$(C_1-C_8)$, Ar, O—Ar, CO—Ar, COO—Ar, PO—Ar$_2$ and PAr$_2$;

where Ar is
an aromatic radical having up to 14 carbon atoms; or
a heteroaromatic, selected from the group consisting of the five-, six- or seven-membered rings having at least one nitrogen, oxygen and/or sulfur atom in the ring;

by reaction of halostyrenes of the formula (IIa) or (IIb)

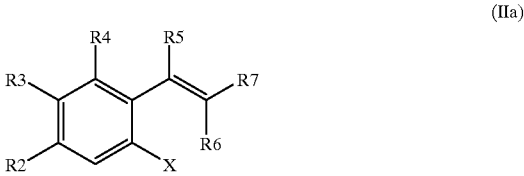

(IIa)

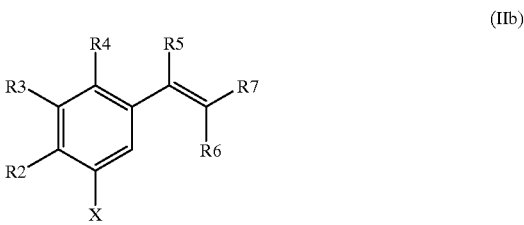

(IIb)

with amines of the formula (III)

$R^1$—$NH_2$ (III)

where in the formulae (IIa), (IIb) and (III)
$R^1$ to $R^7$ have the same meaning as in formula (I);
X is selected from the group consisting of chlorine, bromine, iodine, $OSO_2CF_3$, $OSO_2$aryl-$(C_6-C_{10})$, $OSO_2$alkyl-$(C_1-C_8)$ and $N_2^+Y^-$, where Y is a chlorine, bromine or iodine atom or a tetrafluoroborate or tetraphenylborate anion;

in at least one inert solvent or in water and in the presence of at least one base, selected from the group consisting of
primary, seconary and tertiary alkoxides;
primary and secondary amides of alkali metal and/or alkaline earth metal elements;
alkyl and aryl compounds of alkali metals and/or alkaline earth metals; and
carbonates, hydroxides, hydrogencarbonates of lithium, sodium, potassium, calcium, magnesium and cesium.

According to a preferred embodiment, the radical $R^1$ can be a $(C_1-C_8)$-alkyl, phenyl, naphthyl, anthryl, phenanthryl, biphenyl, pyridine, pyrimidine, oxazole, imidazole, pyrazine, quinoline, indole, furan, benzofuran or thiophene radical.

According to a particularly preferred embodiment of the invention, the radicals $R^2$ to $R^7$ can independently of one another be selected from the group consisting of hydrogen, $(C_1-C_8)$-alkyl, O-alkyl-$(C_1-C_8)$, O—CO-alkyl-$(C_1-C_8)$, N-alkyl$_2$-$(C_1-C_8)$, Ar, F, Cl, $NO_2$, CN, COOH, CHO, $SO_2$-alkyl-$(C_1-C_4)$, NH-alkyl-$(C_1-C_8)$, NH—Ar, NAr$_2$, COO-alkyl-$(C_1-C_8)$, $CONH_2$, CONH-alkyl-$(C_1-C_8)$, CO—$(C_1-C_8)$-alkyl, CO—Ar and/or PO—Ar$_2$; where Ar has the same meaning as described beforehand and is in particular a phenyl radical.

The radicals mentioned beforehand can also be substituted. Particularly preferred cases are those in which
the aromatic radical Ar has up to 5 substitutents;
the heteroaromatic has up to 4 substituents; and/or
the radical $R^1$ has up to 5 substituents,
which independently of one another are selected from the group consisting of fluorine, chlorine, $CF_3$, OH, $NO_2$, CN, $R^5$, O—$R^5$, CHO, CO—$R^5$, COOH, COO—$R^5$, OCO—$R^5$, $SiR^5_3$, $NH_2$, NH—$R^5$, N—$R^5_2$, SO—$R^5$, $SO_2$—$R^5$, $SO_3H$, $SO_3$—$R^5$, $CONH_2$, NHCOH, NHCO—$R^5$, NHCOO—$R^5$, CHCH—$CO_2$-alkyl-($C_1$-$C_8$), PO—$R^5_2$, P—$R^5_2$, $PO_3H_2$, PO(O-alkyl-($C_1$-$C_6$))$_2$ and $CHCHCO_2H$; where $R^5$ is an alkyl radical having 1 to 8 carbon atoms or an aryl radical Ar; where Ar has the same meaning as in claim 1 and is in particular a phenyl radical.

The process according to the invention is particularly suitable for the preparation of dihydroindoles in which the radical $R^1$ is a 4-fluorophenyl or 2-methoxyphenyl radical.

If the radical Ar is a heteroaromatic, up to four further aromatic, heteroaromatic and/or aliphatic rings can be fused to this heteroaromatic ring.

The starting materials necessary for the process, such as amines and 2- or 3-halostyrenes, are commercially available. Specific substituted halostyrenes can be simply prepared by the palladium-catalyzed Heck reaction or Wittig reaction, so that a large number of substrates are available for the process according to the invention.

In view of the generally known fact according to which aryne cyclizations of 2-halophenylethylamines proceed in only moderate yield (R. Huisgen, H. König, Chem. Ber. 1959, 92, 203; R. Huisgen, H. König, N. Bleeker, Chem. Ber, 1959, 92, 424; H. König, R. Huisgen, Chem. Ber. 1959, 92, 429; H. lida, S. Aoyagi, C. Kibayashi, J. Chem. Soc., Perkin I 1975, 2502), it was surprising that according to the process according to the invention any desired substituted 2,3-dihydroindoles can be obtained in good yield in only one stage starting from halostyrene derivatives and primary amines.

The base in the process can be selected from the group consisting of potassium alkoxides, cesium alkoxides, alkali metal amides, organolithium compounds and organomagnesium compounds. Preferentially, the base is selected from the group consisting of potassium tert-butoxide, potassium isopropoxide, sodium methoxide, potassium methoxide, sodium ethoxide, magnesium methoxide, calcium ethoxide, lithium diisopropylamide, lithium diethylamide, sodium dimethylamide, cesium carbonate, butyllithium, phenyllithium, phenylmagnesium chloride and potassium hydroxide.

The inert solvent can be selected from the group consisting of aromatic or aliphatic hydrocarbons, esters, amines and amides. Preferentially, the solvent is selected from the group consisting of THF (tetrahydrofuran), dioxane, diethyl ether, diglyme, MTBE (methyl tert-butyl ether), DME (dimethyl ether), toluene, xylenes, anisole, ethyl acetate, ethylene carbonate and propylene carbonate.

In the process according to the invention, in general the base is employed in an amount from 0.5 to 10 equivalents, based on the halostyrene of the formula (IIa) or (IIb). Preferably, the base is employed in an amount from 0.8 to 5 equivalents, based on the halostyrene of the formula (IIa) or (IIb).

The process according to the invention is customarily carried out at a temperature between 0 and 200° C., preferably between 40 and 180° C., in particular between 60 and 160° C.

For the preparation of indoles according to the present invention, the reaction described beforehand is carried out in the presence of an additional dehydrogenating agent. It is also possible to add a dehydrogenating agent to the reaction mixture after reaction has taken place. The dehydrogenating agent is preferably selected from the group consisting of oxygen, sulfur and DDQ (2,3-dichloro-3,4-dicyanoquinone).

The reaction is in general conducted without pressure, but it can also be carried out at pressures up to 100 bar.

Using the process according to the invention, success has for the first time been achieved in preparing novel 2,3-dihydroindoles selected from the group consisting of N-(2-methoxyphenyl)-2,3-dihydroindole, N-(4-fluorophenyl)-4-chloro-2,3-dihydroindole, N-(4-fluorophenyl)-2,3-dihydroindole and N-(3-ethoxypropyl)-2,3-dihydroindole.

These new dihydroindoles can in particular be used as
a herbicide;
a precursor and/or intermediate for the preparation of dyes, amino acids, photosensitive and/or thermosensitive material, cosmetics;
an antioxidant for cosmetics (in the skin- and haircare field) and oral hygiene products;
an angiotensin(II) antagonist;
a lipoxygenase inhibitor;
a calcium channel blocker, in particular in the treatment of Alzheimer's disease or of depressions;
an inhibitor for enzymes, in particular protein kinase;
a polymerization catalyst, in particular in the preparation of polyesters;
a stabilizer for plastics, in particular for PVC or polyamides;
a ligand for metal catalysts;
a flame-retardant additive; and
an antistatic in plastics.

The examples below serve to illustrate the invention without restricting it.

EXAMPLES

General

The absolute solvents used were stored over molecular sieve 4 Å obtained from Fluka and stored under argon. The amines needed were distilled over $CaH_2$ and stored under an argon atmosphere. The chloroaromatics used in these reactions were degassed repeatedly, saturated with argon and stored over molecular sieve 4 Å. For extraction and purification of reaction products by column chromatography, technical solvents were used which were distilled before use. All reactions were carried out in a 38 ml Ace pressure tube (from Aldrich) under an argon atmosphere with exclusion of air and water.

a) General Working Procedure for Hydroaminations and Aryne Cyclization Reactions with Aromatic amines (In the Following Text GWP1)

2.0 mmol of the halostyrene together with the respective amount of amine are dissolved in 10 ml of toluene in a pressure tube under a protective gas atmosphere. After addition of the base, the sealed reaction vessel is put into an oil bath heated to 135° C. and the reaction mixture is well stirred. After 36 h, the reaction mixture is allowed to cool to room temperature and 20 ml of water are added with stirring. The aqueous phase is extracted three times with methylene chloride. After the combined organic phases have been dried over magnesium sulfate, the solvent is removed in vacuo. The crude product thus obtained is purified by column chromatography using the solvent indicated and is characterized by means of NMR and mass-spectroscopic investigations.

The numbering of the carbon atoms in the formulae relates to the NMR assignment.

Example 1

N-Phenyl-2,3-dihydroindole

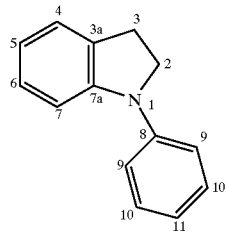

Starting materials: 0.28 g (2.0 mmol) of 2-chlorostyrene, 0.28 g (3.0 mmol) of aniline, 0.67 g (6.0 mmol) of potassium tert-butoxide.

Eluent: Hexane:

Yield: 0.21 g (53% of theory).

$^1$H-NMR (360 MHz, 25° C., CDCl$_3$): δ=7.32 (dd, 3JHH=8.0 Hz, 3JHH=7.1 Hz, 2H, 10-H), 7.21 (d, $^3J_{HH}$=8.0 Hz, 2H, 9-H), 7.14 (d, $^3J_{HH}$=7.1 Hz, 1H, 4-H), 7.12 (d, $^3J_{HH}$=8.0 Hz, 1H, 7-H), 7.05 (dd , $^3J_{HH}$=8.0 Hz, $^3J_{HH}$=7.5 Hz, 1H, 6-H), 6.94 (t, $^3J_{HH}$=7.1 Hz, 1H, 11-H), 6.73 (dd, $^3J_{HH}$=7.5 Hz, $^3J_{HH}$=7.1 Hz, 1H, 5-H), 3.92 (t, $^3J_{HH}$=8.4 Hz, 2H, 2-H), 3.10 (t, $^3J_{HH}$=8.4 Hz, 2H, 3-H).

$^{13}$C{$^1$H}-NMR (90 MHz, 25° C., CDCl$_3$): δ=147.1 (C8), 144.2 (C7a), 131.2 (C3a), 129.1 (C10), 127.1 (C4), 125.0 (C6), 120.9 (C5), 118.8 (C7), 117.7 (C9), 108.2 (C11), 52.1 (C2), 28.2 (C3).

MS (70 eV): m/e=195 (M$^+$), 165, 116, 91, 77.

Example 2

N-(4-Fluorophenyl)-2,3-dihydroindole

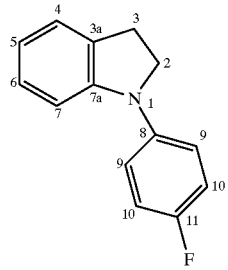

Starting materials: 0.28 g (2.0 mmol) of 2-chlorostyrene, 0.33 g (3.0 mmol) of 4-fluoroaniline, 0.67 g (6.0 mmol) of potassium tert-butoxide.

Eluent: Hexane

Yield: 0.23 g (54% of theory).

$^1$H-NMR (360 MHz, 25° C., CDCl$_3$): δ=7.19–6.95 (m, 7H, HAr), 6.73 (dd, $^3J_{HH}$=7.5 Hz, $^3J_{HH}$=7.1 Hz, 1H, 5-H), 3.85 (t, $^3J_{HH}$=8.4 Hz, 2H, 2-H), 3.08 (t, $^3J_{HH}$=8.4 Hz, 2H, 3-H).

$^{13}$C{$^1$H}-NMR (90 MHz, 25° C., CDCl$_3$): δ=157.7 (d, $^1J_{CF}$=241.1 Hz, C11), 147.6 (C7a), 140.51 (C8), 130.9 (C3a), 127.1 (C4), 125.0 (C6), 119.8 (d, $^3J_{CF}$=8.4 Hz, C9), 118.8 (C5), 115.7 (d, $^2J_{CF}$=21.1 Hz C10), 107.6 (C7), 52.7 (C2), 28.2 (C3).

MS (70 eV): m/e=213 (M$^+$), 183, 165, 116, 105, 91.

Example 3

N-(2-Methoxyphenyl)-2,3-dihydroindole

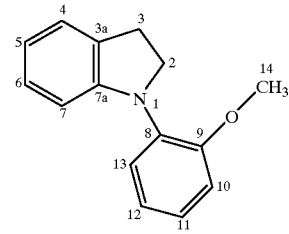

Starting materials: 0.28 g (2.0 mmol) of 2-chlorostyrene, 0.37 g (3.0 mmol) of o-anisidine, 0.67 g (6.0 mmol) of potassium tert-butoxide.

Eluent: (ethyl acetate/hexane=1/50).

Yield: 0.26 g (58% of theory).

$^1$H-NMR (360 MHz, 25° C., CDCl$_3$): δ=7.35 (d, $^3J_{HH}$=7.5 Hz, 13-H), 7.15–7.11 (m, 2H, 4-H/7-H), 7.10–9.90 (m, 3H, 5-H/6-H/12-H), 6.68 (dd, $^3J_{HH}$=8.0 Hz, $^3J_{HH}$=7.5 Hz, 1H, 11-H), 6.46 (d, $^3J_{HH}$=8.0 Hz, 10-H), 3.88 (t, $^3J_{HH}$=8.4 Hz, 2H, 2-H), 3.84 (s, 3H, 14-H), 3.14 (t, $^3J_{HH}$=8.4 Hz, 2H, 3-H).

$^{13}$C{$^1$H}-NMR (90 MHz, 25° C., CDCl$_3$): δ=154.5 (C9), 149.6 (C7a), 134.0 (C3a), 130.2 (C8), 126.9 (CH), 125.3 (CH), 124.6 (CH), 123.3 (CH), 121.0 (CH), 118.0 (CH), 112.3 (CH), 109.0 (CH), 55.5 (C14), 53.5 (C2), 28.8 (C3).

MS (70 eV): m/e=225 (M$^+$), 210(M$^+$—CH$_3$), 194, 180, 165, 152.

Example 4

N-(4-Fluorophenyl)-4chloro-2,3-dihydroindole

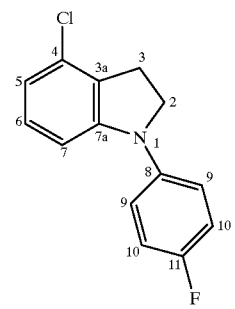

Starting materials: 0.35 g (2.0 mmol) of 2,6-dichlorostyrene, 0.28 g (2.5 mmol) of 4-fluoroaniline, 0.34 g (3.0 mmol) of potassium tert-butoxide.

Eluent: Hexane.

Yield: 0.26 g (50% of theory).

$^1$H-NMR (360 MHz, 25° C., CDCl$_3$): δ=7.12–6.64 (m, 7H, HAr), 3.88 (t, $^3J_{HH}$=8.4 Hz, 2H, 2-H), 3.10 (t, $^3J_{HH}$=8.4 Hz, 2H, 3-H).

$^{13}$C{$^1$H}-NMR (90 MHz, 25° C., CDCl$_3$): δ=157.8 (d, $^1J_{CF}$=241.2 Hz, C11), 149.1 (C7a), 140.0 (C8), 131.0 (C4), 128.9 (C3a), 128.7 (C6), 120.4 (d, $^3J_{CF}$=6.9 Hz, C9), 118.7 (C5), 115.9 (d, $^2J_{CF}$=22.1 Hz, C10), 105.7 (C7), 52.5 (C2), 27.5 (C3).

MS (70 eV): m/e=247 (M$^+$), 211 (M$^+$—HCl), 183, 105, 89.

b) General Working Procedure for Hydroaminations and Aryne Cyclization Reactions with Aliphatic Amines (In the Following Text GWP2)

6.0 mmol of amine are dissolved in 12 ml of THF in a 38 ml Ace pressure tube (from Aldrich) under a protective gas atmosphere and the solution is cooled to −78° C. After addition of 10 mol % of n-BuLi solution, 4.0 mmol of 3-chlorostyrene are added and the sealed reaction vessel is stirred at −30° C. for 4 h before it is allowed to warm to room temperature. The solvent is then removed in vacuo, the residue is taken up in 12 ml of toluene, and the mixture is treated with the amount of potassium tert-butoxide indicated and put into an oil bath preheated to 135° C. The reaction mixture is well stirred and, after 36 h, is allowed to cool to room temperature and 20 ml of water are added with stirring. The aqueous phase is extracted three times with methylene chloride. After the combined organic phases have been dried over magnesium sulfate, the solvent is removed in vacuo. The crude product thus obtained is purified by column chromatography using the solvent indicated.

Example 5

N-Butyl-2,3-dihydroindole

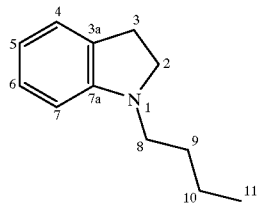

Starting materials: 0.55 g (4.0 mmol, 0.51 ml) of 3-chlorostyrene, 0.44 g (6.0 mmol, 0.60 ml) of n-butylamine, 10 mol % of n-BuLi solution (1.6 M in hexane), 1.35 g (12.0 mmol) of potassum tert-butoxide.

Eluent: hexane/ethyl acetate (5:1).

Yield: 53% of theory $^1$H-NMR (400 MHz, 25° C., CDCl$_3$): δ=6.94 (m, 2H, 4-H, 6-H), 6.53 (t, $^3J_{HH}$=7.5 Hz, 1H, 5-H), 6.38 (d, $^3J_{HH}$=8.0 Hz, 1H, 7-H), 3.23 (t, $^3J_{HH}$=7.5 Hz, 2H, 2-H), 2.96 (t, $^3J_{HH}$=7.5 Hz, 2H, 3-H), 2.84 (t, $^3J_{HH}$=7.5 Hz, 2H, 8-H), 1.52 (q, $^3J_{HH}$=7.5 Hz, 2H, 9-H), 1.31 (sextet, $^3J_{HH}$=7.5 Hz, 2H, 10-H), 0.96 (t, $^3J_{HH}$=7.5 Hz, 3H, 11 -H).

$^{13}$C{$^1$H}-NMR (100 MHz, 25° C., CDCl$_3$): δ=152.1 (C7a), 129.3 (C3a), 127.7 (C4), 126.6 (C6), 116.5 (C5), 106.2 (C7), 52.4 (C2), 48.3 (C8), 27.9 (C3), 22.0 (C9), 19.8 (C10), 13.3 (C11).

MS (70 eV): m/e=175 (M$^+$), 132 (M$^+$—C$_3$H$_7$), 117, 91, 77.

Example 6

N-(3-Ethoxypropyl)-2,3-dihydroindole

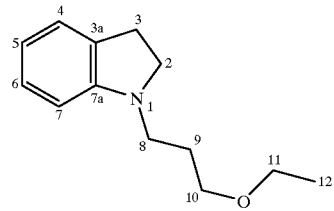

Starting materials: 0.55 g (4.0 mmol, 0.51 ml) of 3-chlorostyrene, 0.62 g (6.0 mmol, 0.72 ml) of 3-ethoxypropylamine, 10 mol % of n-BuLi solution (1.6 M in hexane), 1.35 g (12.0 mmol) of potassium tert-butoxide.

Eluent: hexane/ethyl acetate (5:1).

Yield: 53% of theory $^1$H-NMR (400 MHz, 25° C., CDCl$_3$): δ=6.94 (m, 2H, 4-H, 6-H), 6.53 (t, $^3J_{HH}$=7.5 Hz, 1H, 5-H), 6.38 (d, $^3J_{HH}$=8.0 Hz, 1H, 7-H), 3.23 (t, $^3J_{HH}$=7.5 Hz, 2H, 2-H), 2.96 (t, $^3J_{HH}$=7.5 Hz, 2H, 3-H), 2.84 (t, $^3J_{HH}$=7.5 Hz, 2H, 8-H), 1.52 (q, $^3J_{HH}$=7.5 Hz, 2H, 9-H), 1.31 (sextet, $^3J_{HH}$=7.5 Hz, 2H, 10-H), 0.96 (t, $^3J_{HH}$=7.5 Hz, 3H, 11-H), $^{13}$C{$^1$H}-NMR (100 MHz, 25° C., CDCl$_3$): δ=152.1 (C7a), 129.3 (C3a), 127.7 (C4), 126.6 (C6), 116.5 (C5), 106.2 (C7), 52.4 (C2), 48.3 (C8), 27.9 (C3), 22.0 (C9), 19.8 (C10), 13.3 (C11).

MS (70 eV): m/e=205 (M$^+$), 132 (M$^+$—CH$_2$CH$_2$—OEt), 117, 103, 91, 77.

Example 7

N-(2-Phenylethyl)-2,3-dihydroindole

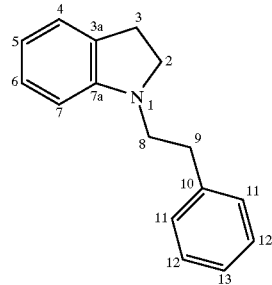

Starting materials: 0.55 g (4.0 mmol, 0.51 ml) of 3-chlorostyrene, 0.73 g (6.0 mmol, 0.76 ml) of 2-phenylethylamine, 10 mol % of n-BuLi solution (1.6 M in hexane), 1.35 g (12.0 mmol) of potassium tert-butoxide.

Eluent: hexane/ethyl acetate (5:1).

Yield: 53% of theory $^1$H-NMR (400 MHz, 25° C., CDCl$_3$): δ=6.94 (m, 2H, 4-H, 6-H), 6.53 (t, $^3J_{HH}$=7.5 Hz, 1H, 5-H), 6.38 (d, $^3J_{HH}$=8.0 Hz, 1H, 7-H), 3.23 (t, $^3J_{HH}$=7.5 Hz, 2H, 2-H), 2.96 (t, $^3J_{HH}$=7.5 Hz, 2H, 3-H), 2.84 (t, $^3J_{HH}$=7.5 Hz, 2H, 8-H), 1.52 (q, $^3J_{HH}$=7.5 Hz, 2H, 9-H), 1.31 (sextet, $^3J_{HH}$=7.5 Hz, 2H, 10-H), 0.96 (t, $^3J_{HH}$=7.5 Hz, 3H, 11-H).

$^{13}$C{$^1$H}-NMR (100 MHz, 25° C., CDCl$_3$): δ=152.1 (C7a), 129.3 (C3a), 127.7 (C4), 126.6 (C6), 116.5 (C5), 106.2 (C7), 52.4 (C2), 48.3 (C8), 27.9 (C3), 22.0 (C9), 19.8 (C10), 13.3 (C11).

MS (70 eV): m/e=223 (M$^+$), 132 (M$^+$—CH$_2$—Ph), 117, 103, 77.

Example 8

N-(tert-Butyl)-2,3-dihydroindole

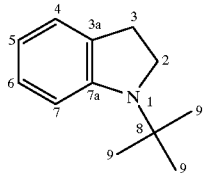

Starting materials: 0.55 g (4.0 mmol, 0.51 ml) of 3-chlorostyrene, 0.44 g (6.0 mmol, 0.63 ml) of tert-butylamine, 10 mol % of n-BuLi solution (1.6 M in hexane), 1.35 g (12.0 mmol) of potassium tert-butoxide.

Eluent: hexane/ethyl acetate (5:1).

Yield: 53% of theory $^1$H-NMR (400 MHz, 25° C., CDCl$_3$): δ=6.94 (m, 2H, 4-H, 6-H), 6.53 (t, $^3J_{HH}$=7.5 Hz, 1H, 5-H), 6.38 (d, $^3J_{HH}$=8.0 Hz, 1H, 7-H), 3.23 (t, $^3J_{HH}$=7.5 Hz, 2H, 2-H), 2.96 (t, $^3J_{HH}$=7.5 Hz, 2H, 3-H), 2.84 (t, $^3J_{HH}$=7.5 Hz, 2H, 8-H), 1.52 (q, $^3J_{HH}$=7.5 Hz, 2H, 9-H), 1.31 (sextet, $^3J_{HH}$=7.5 Hz, 2H, 10-H), 0.96 (t, $^3J_{HH}$=7.5 Hz, 3H, 11-H).

$^{13}$C{$^1$H}-NMR (100 MHz, 25° C., CDCl$_3$): δ=152.1 (C7a), 129.3 (C3a), 127.7 (C4), 126.6 (C6), 116.5 (C5), 106.2 (C7), 52.4 (C2), 48.3 (C8), 27.9 (C3), 22.0 (C9), 19.8 (C10), 13.3 (C11).

MS (70 eV): m/e=176 (M$^+$), 161 (M$^+$—CH$_3$), 120 (M$^+$—(CH$_3$)$_2$—C=CH$_2$), 105, 91, 77.

c) General Working Procedure for the Preparation of Indoles from 2,3-dihydroindolines (In the Following Text GWP3)

After the preparation of the 2,3-dihydroindolines according to GWP1 (but using 2.0 mmol of 3-chlorostyrene and 4.0 mmol of amine), the reaction solution is in each case directly reacted further without isolating the 2,3-dihydroindoline. To this end, the reaction mixture is allowed to cool to room temperature and is treated with 2.0 mmol of DDQ. The suspension is allowed to react for a further 20 h at an oil bath temperature of 120° C. with vigorous stirring. After cooling to room temperature, the brown solution is mixed with 20 ml of water. The aqueous phase is extracted three times with methylene chloride. After the combined organic phases have been dried over magnesium sulfate, the solvent is removed in vacuo. The crude product thus obtained is purified by column chromatography using the eluent indicated.

Example 9

N-4-Biphenylindole

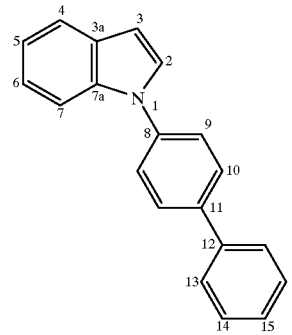

Starting materials: 0.27 g (2.0 mmol, 0.26 ml) of 3-chlorostyrene, 0.67 g (4.0 mmol) of 4-phenylaniline, 0.67 g (6.0 mmol) of potassium tert-butoxide, 0.45 g (2.0 mmol) of DDQ.

Eluent: hexane.

Yield: 0.35 g ( 65% of theory).

$^1$H-NMR (360 MHz, 25° C., CDCl$_3$): δ=7.63–7.26 (m, 5H, arom. H), 7.10 (m, 1H, 6-H), 7.01 (m, 8H, arom. H), 6.45 (4, $^3J_{HH}$=8.0 Hz, 1H, 3-H).

$^{13}$C{$^1$H}-NMR (90 MHz, 25° C., CDCl$_3$): δ=143.1 (C-8), 137.4 (C-7a), 137.2 (C-12), 129.8 (C-3a), 129.6 (C-14), 127.5 (C-15), 127.4 (C-13), 127.3 (C-10), 126.3 (C-11), 125.0 (C-2), 122.3 (C-5), 120.5 (C-4), 120.0 (C-6), 118.2 (C-9), 110.7 (C-7), 104.1 (C-3).

MS (70eV): m/e=269 (M$^+$-phenyl), 134, 119, 89.

What is claimed is:

1. A 2,3-dihydroindole which is selected from the group consisting of N-(4-fluorophenyl)-4-chloro-2,3-dihydroindole, N-(4-fluorophenyl)-2,3-dihydroindole and N-(3-ethoxypropyl)-2,3-dihydroindole.
2. A ligand metal catalyst wherein the ligands are a 2,3-dihydroindole according to claim 1.
3. A cosmetic or oral hygiene composition which comprises the cosmetic or oral hygiene product and a 2,3-dihydroindole in claim 1 as an antioxidant.
4. A flame-retardant additive which comprises a 2,3-dihydroindole according to claim 1.
5. A method for killing unwanted plant growth which comprises applying a 2,3-dihydroindole as claimed in claim 1 to said plant or to an area where it resides.
6. A plastic which comprises a 2,3-dihydroindole according to claim 1 as a stabilizing agent or an antistatic agent.
7. A method for inhibiting angiotensin (II) in a host in need thereof which comprises administering a 2,3-dihydroindole according to claim 1 to said host.
8. A method for inhibiting lipoxygnase in a host in need thereof, which comprises administering a 2,3-dihydroindole according to claim 1 to said host.
9. A method for blocking a calcium channel in a host in need thereof, which comprises administering a 2,3-dihydroindole according to claim 1 to said host.
10. A method for treating depression in a host in need thereof, which comprises administering a 2,3-dihydroindole according to claim 1 to said host.
11. A method for treating Alzheimer's disease to a host in need thereof, which comprises administering a 2,3-dihydroindole according to claim 1 to said host.
12. A method for inhibiting protein kinase in a host in need thereof, which comprises administering a 2,3-dihydroindole according to claim 1 to said host.

13. In a method for preparing polyesters, the improvement which comprises adding a 2,3-dihydroindole according to claim 1 as a polymerization catalyst.

14. A method for stabilizing a plastic which comprises adding a 2,3-dihydroindole according to claim 1 to said plastic.

15. The method according to claim 14, wherein the plastic is a PVC or a polyamide.

16. A method for reducing the static in a plastic which comprises adding a 2,3-dihydroindole according to claim 1 as an antistatic agent to said plastic.

17. A process for the preparation of 2,3-dihydroindoles of the formula (I)

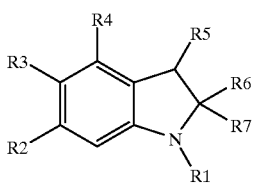

(I)

in which the radicals R1 to R7 independently of one another are selected from the group consisting of hydrogen, fluorine, chlorine, $(C_1–C_8)$-alkyl, O-alkyl-$(C_1–C_8)$, OCO-alkyl-$(C_1–C_8)$, OH, $NO_2$, Si(alkyl)$_3$-$(C_1–C_8)$, $CF_3$, CN, COOH, CHO, $SO_3H$, $NH_2$, NH-alkyl-$(C_1–C_8)$, N-alkyl$_2$-$(C_1–C_8)$, NH—Ar, NAr$_2$, P-alkyl$_2$-$(C_1–C_8)$, $SO_2$-alkyl-$(C_1–C_6)$, SO-alkyl-$(C_1–C_6)$, NHCO-alkyl-$(C_1–C_4)$, COO-alkyl-$(C_1–C_8)$, $CONH_2$, CONH-alkyl-$(C_1–C_8)$, CO-alkyl-$(C_1–C_8)$, NHCOH, NHCOO-alkyl-$(C_1–C_4)$, CHCH—$CO_2$-alkyl-$(C_1–C_8)$, CHCHCO$_2$H, P-alkyl$_2$-$(C_1–C_8)$, POalkyl$_2$-$(C_1–C_4)$, $PO_3H_2$, PO(O-alkyl-$(C_1–C_6)$)$_2$, $SO_3$-alkyl-$(C_1–C_4)$, $SO_2$-alkyl-$(C_1–C_6)$, SO-alkyl-$(C_1–C_6)$, Si(alkyl)$_3$-$(C_1–C_8)$, Ar, O—Ar, CO—Ar, COO—Ar, PO—Ar$_2$ and PAr$_2$;

where Ar is
an aromatic radical having up to 14 carbon atoms; or
a heteroaromatic, selected from the group consisting of the five-, six- or seven-membered rings having at least one nitrogen, oxygen and/or sulfur atom in the ring;

by reaction of halostyrenes of the formula (IIa) or (IIb)

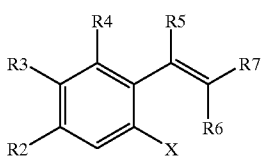

(IIa)

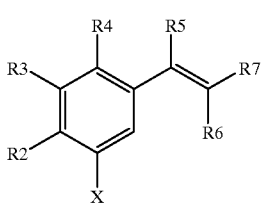

(IIb)

with amines of the formula (III)

(III)

where in the formulae (IIa), (IIb) and (III)

$R^1$ to $R^7$ have the same meaning as in formula (I);
X is selected from the group consisting of chlorine, bromine, iodine, $OSO_2CF_3$, $OSO_2$aryl-$(C_6–C_{10})$, $OSO_2$alkyl-$(C_1–C_8)$ and $N_2^+Y^-$, where Y is a chlorine, bromine or iodine atom or a tetrafluoroborate or tetraphenylborate anion;

in at least one inert solvent or in water and in the presence of at least one base, selected from the group consisting of
primary, seconary and tertiary alkoxides;
primary and secondary amides of alkali metal and/or alkaline earth metal elements;
alkyl and aryl compounds of alkali metals and/or alkaline earth metals; and
carbonates, hydroxides, hydrogencarbonates of lithium, sodium, potassium, calcium, magnesium and cesium.

18. The process as claimed in claim 17, wherein the radical $R^1$ is a $(C_1–C_8)$-alkyl, phenyl, naphthyl, anthryl, phenanthryl, biphenyl, pyridine, pyrimidine, oxazole, imidazole, pyrazine, quinoline, indole, furan, benzofuran or thiophene radical.

19. The process as claimed in claim 17, wherein the radicals $R^2$ to $R^7$ independently of one another are selected from the group consisting of hydrogen, $(C_1–C_8)$-alkyl, O-alkyl-$(C_1–C_8)$, OCO-alkyl-$(C_1–C_8)$, N-alkyl$_2$-$(C_1–C_8)$, Ar, F, Cl, $NO_2$, CN, COOH, CHO, $SO_2$-alkyl-$(C_1–C_4)$, NH-alkyl-$(C_1–C_8)$, NH—Ar, NAr$_2$, COO-alkyl-$(C_1–C_8)$, $CONH_2$, CONH-alkyl-$(C_1–C_8)$, CO-alkyl-$(C_1–C_8)$, CO—Ar and/or PO—Ar$_2$; where Ar has the same meaning as in claim 1 and is in particular a phenyl radical.

20. The process as claimed in claim 17, wherein
the aromatic radical Ar has up to 5 substituents;
the heteroaromatic has up to 4 substituents; and/or
the radical $R^1$ has up to 5 substituents,
which independently of one another are selected from the group consisting of fluorine, chlorine, $CF_3$, OH, $NO_2$, CN, $R^5$, O—$R^5$, CHO, CO—$R^5$, COOH, COO—$R^5$, OCO—$R^5$, SiR$^5$$_3$, $NH_2$, NH—$R^5$, N—$R^5$$_2$, SO—$R^5$, $SO_2$—$R^5$, $SO_3H$, $SO_3$—$R^5$, $CONH_2$, NHCOH, NHCO—$R^5$, NHCOO—$R^5$, CHCH—$CO_2$-alkyl-$(C_1–C_8)$, PO—$R^5$$_2$, P—$R^5$$_2$, $PO_3H_2$, PO(O-alkyl-$(C_1–C_6)$)$_2$ and CHCHCO$_2$H; where $R^5$ is an alkyl radical having 1 to 8 carbon atoms or an aryl radical Ar; where Ar has the same meaning as in claim 1 and is in particular a phenyl radical.

21. The process as claimed in claim 17, wherein $R^1$ is a 4-fluorophenyl or 2-methoxyphenyl radical.

22. The process as claimed in claim 17, wherein the radical Ar is a heteroaromatic to whose heteroaromatic ring up to four further aromatic, heteroaromatic and/or aliphatic rings are fused.

23. The process as claimed in claim 17, wherein the base is selected from the group consisting of potassium alkoxides, cesium alkoxides, alkali metal amides, organolithium compounds and organomagnesium compounds.

24. The process as claimed in claim 23, wherein the base is selected from the group consisting of potassium tert-butoxide, potassium isopropoxide, sodium methoxide, potassium methoxide, sodium ethoxide, magnesium methoxide, calcium ethoxide, lithium diisopropylamide, lithium diethylamide, sodium dimethylamide, cesium carbonate, butyllithium, phenyllithium, phenylmagnesium chloride and potassium hydroxide.

25. The process as claimed in claim 17, wherein the inert solvent is selected from the group consisting of aromatic or aliphatic hydrocarbons, esters, amines and amides.

26. The process as claimed in claim 25, wherein the solvent is selected from the group consisting of THF, dioxane, diethyl ether, diglyme, MTBE, DME, toluene, xylenes, anisole, ethyl acetate, ethylene carbonate and propylene carbonate.

27. The process as claimed in claim 17, wherein the base is employed in an amount from 0.5 to 10 equivalents, based on the halostyrene of the formula (IIa) or (IIb).

28. The process as claimed in claim 27, wherein the base is employed in an amount from 0.8 to 5 equivalents, based on the halostyrene of the formula (IIa) or (IIb).

29. The process as claimed in claim 17, wherein the reaction is carried out at a temperature between 0 and 200° C., preferably between 40 and 180° C., in particular between 60 and 160° C.

30. The process as claimed in claim 17, wherein the reaction is carried out in the presence of an additional dehydrogenating agent.

31. The process as claimed in claim 17, wherein a dehydrogenating agent is added to the reaction mixture after reaction has taken place.

32. The process as claimed in claim 30, wherein the dehydrogenating agent is selected from the group consisting of oxygen, sulfur and DDQ.

33. In a process for preparing a dye, amino acid, a photosensitive and/or thermosensitive material, or a cosmetic, the improvement which comprises using a 2,3-dihydroindole as claimed in claim 1 in said process.

* * * * *